United States Patent [19]

Fuchs et al.

[11] 4,400,515

[45] Aug. 23, 1983

[54] QUINACRIDONE MIXTURES, PROCESS FOR THEIR MANUFACTURE AND THEIR USE AS PIGMENTS

[75] Inventors: Otto Fuchs, Frankfurt am Main; Adolf Kroh, Selters, both of Fed. Rep. of Germany

[73] Assignee: Hoechst Aktiengesellschaft, Frankfurt am Main, Fed. Rep. of Germany

[21] Appl. No.: 237,505

[22] Filed: Feb. 23, 1981

Related U.S. Application Data

[63] Continuation of Ser. No. 79,592, Sep. 27, 1979, abandoned.

[30] Foreign Application Priority Data

Sep. 29, 1978 [DE]  Fed. Rep. of Germany ....... 2842468

[51] Int. Cl.$^3$ .............................................. C09B 48/00
[52] U.S. Cl. .................................. 546/57; 106/288 Q
[58] Field of Search ...................... 546/57; 106/288 Q

[56] References Cited

U.S. PATENT DOCUMENTS

| | | | |
|---|---|---|---|
| 3,741,970 | 6/1973 | Fuchs | 546/57 |
| 3,749,726 | 7/1973 | Fuchs et al. | 546/57 |
| 3,836,379 | 9/1974 | Kirsch et al. | 546/57 X |

FOREIGN PATENT DOCUMENTS

| | | | |
|---|---|---|---|
| 1960896 | 6/1971 | Fed. Rep. of Germany | 546/57 |
| 1960897 | 6/1971 | Fed. Rep. of Germany | 546/57 |

*Primary Examiner*—Donald G. Daus
*Assistant Examiner*—Diana G. Rivers
*Attorney, Agent, or Firm*—Curtis, Morris & Safford

[57] ABSTRACT

Compositions of linear trans-quinacridones containing at least one component (I) selected from unsubstituted, chloro- and methyl-substituted quinacridone and at least one component (II) selected from bis-(carbamoyl)-quinacridones, the carbamoyl groups of which are unsubstituted, N-mono-alkyl substituted or N,N-dialkyl-substituted, are pigments useful for coloring plastics and especially lacquers. These compositions are preferably prepared by joint ring closure of the corresponding 2,5-dianilino-terephthalic acids or esters.

18 Claims, No Drawings

QUINACRIDONE MIXTURES, PROCESS FOR THEIR MANUFACTURE AND THEIR USE AS PIGMENTS

This is a continuation of application Ser. No. 79,592, filed Sept. 27, 1979, now abandoned.

The present invention relates to mixtures of compounds comprising at least one component of the formula (I)

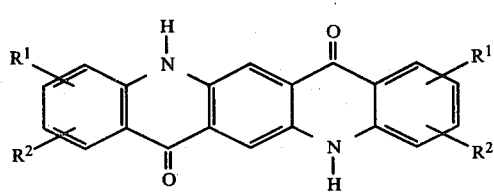

wherein $R^1$ and $R^2$ are the same or different and stand for hydrogen, chlorine or methyl, and at least one component of the formula (II)

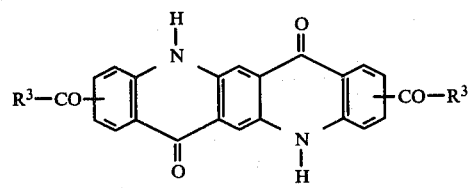

wherein $R^3$ is $-NH-R^4$ or $-N(R^5)_2$ with $R^4$ being hydrogen or alkyl of 1 to 6 carbon atoms and $R^5$ being methyl or ethyl, to a process for their manufacture and to their use as pigments.

The term "mixtures" includes also solid solutions of compounds of the formulae I and II.

The compounds of the formula I are known. They can be prepared by cyclization of compounds of the formula (III)

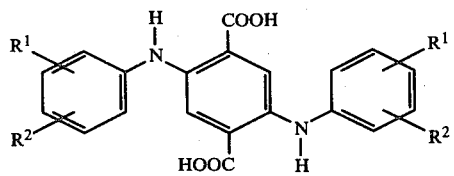

in the presence of acid condensation agents (cf. French Pat. Nos. 1,226,825 and 1,233,785; Belgian Pat. No. 611,271; Austrian Pat. No. 218,651). Naturally only one of the radicals $R^1$ and $R^2$ of said formula can be in orthoposition with regard to the amino nitrogen, since one proton in ortho-position is split off in the cyclization. When both ortho-positions are unsubstituted, cyclization produces up to three isomers in the case of monosubstitution, in metaposition, in the case of disubstitution in meta, para position and in the case of disubstitution in meta, meta position with different substituents. For example, the cyclization of the meta-chlorine derivative yields a mixture of 3,10-, 1,8- and 1,10-dichloroquinacridone.

Analogously, the 3,4-dichloroaniline derivative yields a mixture of 2,3,9,10-, 2,3,8,9- and 1,2,8,9-tetrachloroquinacridone.

Some of the compounds of formula II are known from German Pat. Nos. 1,960,896 and 1,960,897. The compounds not disclosed in these publications can be prepared in analogous manner. In this case, too, isomers are obtained when $-CO-R^3$ in the analogous starting compound of formula IV

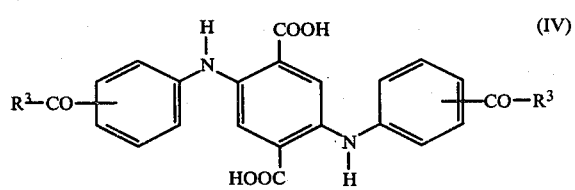

is in the meta-position with regard to nitrogen.

In any case the quinacridones can alternatively be prepared with lower alkyl esters of these terephthalic acids, instead of the acids as such, preferably the methyl and the ethyl esters.

The mixtures according to the invention can be obtained by intimately mixing the components, but preferably are prepared by simultaneous cyclization of the compounds of the formulae III and IV or of the corresponding alkyl esters.

Hence, the present invention also relates to a process for the preparation of the mixtures according to the invention, which comprises heating mixtures of compounds of the formulae III and IV or alkyl esters of these compounds having alkyl radicals with from 1 to 4 carbon atoms, in the presence of acid condensation agents. Naturally several compounds of the formulae III and/or IV can likewise be submitted to this simultaneous cyclization. Preferred embodiments of this preparation process will be described in detail hereinunder:

A mixture consisting of from 30 to 95, preferably 50 to 95, parts by weight of a compound or compounds III and of from 5 to 70, preferably 5 to 50, parts by weight of a compound or compounds IV is heated in the presence of acid condensation agents. Heating is preferably carried out without the addition of diluents, in 2.5 to 10 times, in particular in 2.5 to 5 times, the quantity of polyphosphoric acid or an acidic lower polypolyphosphoric acid alkyl ester, this quantity being calculated on the weight of the compounds III and IV, to a temperature from 80° to 150° C., in particular from 100° to 135° C. The polyphosphoric acid preferably has a $P_2O_5$ content of at least 81.5%. The preferred acidic polyphosphoric acid ester is a methyl ester having a $P_2O_5$ content of at least 79.5%.

The melt of the cyclization product is thereafter hydrolyzed in water and, the precipitated quinacridone mixture is isolated, for example by filtration, and suitably washed to neutral with water. The water-moist crude quinacridone mixture is thereafter submitted to a treatment with organic solvents, or with mixtures of solvent and water, at a temperature of from 40° to 150° C., preferably 70° to 135° C., to convert it into an optimum pigment form.

Suitable solvents for this purpose are those as described for example in German Pat. No. 1,262,106. However, preferred solvents are those that can be easily regenerated practically quantitatively from the pigment suspension after the treatment by simple distillation and that can be reused directly or after purification. Suitable solvents for this mode of operating are lower alcohols and ketones, for example methanol, ethanol, propanol, isopropanol, butanol, isobutanol, acetone, methylethylketone and methylisobutylketone.

The properties of the pigment may be influenced favorably by wet grinding of the suspension of solvent, water and crude quinacridone, prior to or after the treatment at 40° to 150° C. Suitable wet grinding mills are colloid mills such as PUC mills, toothed attrition mills, agitator ball mills and similarly acting devices. The properties of the pigments may moreover be influenced favorably by the addition of surfactants and of resins or waxes during the hydrolysis of the cyclization product and/or during the solvent treatment of the crude quinacridone.

The composition of the present invention suitably comprises 30 to 95%, preferably 50 to 95%, by weight of at least one component I of the formula

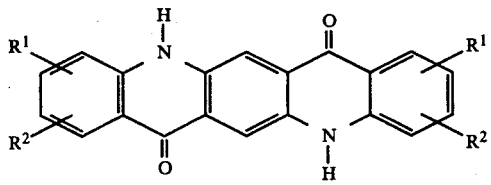

and 5 to 70%, preferably 5 to 50%, by weight of at least one component II of the formula

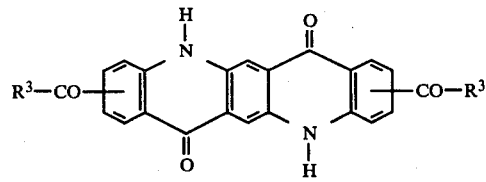

Examples of compositions in accordance with the claimed invention are as follows: 85% by weight of 2,9-dimethylquinacridone and 15% by weight of 2,9-bis-(carbamoyl)-quinacridone; about 66.7% by weight of 2,9-dimethyl-quinacridone and about 33.3% by weight of 2,9-bis-(N-n-hexylcarbamoyl)-quinacridone; about 59% of 2,9-dimethyl-quinacridone and about 41% of 2,9-bis-(N-n-butyl-carbamoyl)-quinacridone; about 66.7% by weight of 2,9-dimethyl-quinacridone and about 33.3% by weight of 2,9-bis-(N-ethyl-carbamoyl)-quinacridone; about 66.7% by weight of 2,9-dimethyl-quinacridone and about 33.3% by weight of 2,9-bis-(N,N-dimethyl-carbamoyl)-quinacridone; about 84.5% by weight of 2,9-dimethyl-quinacridone and about 15.5% by weight of a mixture of 3,10-, 1,8- and 1,10-bis-(N-methyl-carbamoyl)- quinacridone as obtained by ring closure of 2,5,-bis-m-(N-methyl-carbamoyl)-anilino terephthalic acid; and 94% by weight of 2,9-dimethyl-quinacridone and 6% by weight of 2,9-bis-(carbamoyl)-quinacridone.

The quinacridone mixtures according to the invention can be used as pigments. They give lacquer coatings of a high transparency and they are distinguished by excellent rheological properties, for example a low viscosity in lacquer systems. The fastness properties, in particular to light and to weathering, are at least equal to or superior to those of known quinacridones. Hence, the pigments according to the invention are suitable for use in the automobile field and in similar fields, where pigments of high transparency are required.

The combination of high tinctorial strength and high transparency, which generally are due to a fine division of the pigment particles, with good rheological properties in the application medium is astonishing, since fine pigment particles usually involve a high absorption of binding agent and, consequently, a high viscosity of lacquers made with the pigment particles. Therefore, the pigments according to the invention are especially suitable for metallic lacquers. Moreover they may be used for the pigmentation of plastics because of the good processability of these pigments.

The following examples illustrate the invention. Parts and percentages are by weight. Temperatures are indicated in degrees Celsius (centigrade).

EXAMPLE 1

A mixture of 100 parts of 2,5-di-(4'-methylphenylamino)-terephthalic acid and 50 parts of 2,5-di-(4'-dimethylcarbamoyl-phenylamino)-terephthalic acid is added while stirring to 450 parts of an acidic polyphosphoric acid methyl ester ($P_2O_5$ content about 80%), at 110° to 120°, in 1 hour. Stirring is continued for 2 hours at 125° to 130°, whereupon the melt is hydrolyzed by pouring it into 1,350 parts of 70°-hot water, while stirring. The precipitated crude quinacridone is filtered off and washed to neutral with water.

The neutral moist crude quinacridone is stirred into 900 parts of isobutanol (80%) and thereafter water is added until the total weight of the mixture is 1500 parts. The suspension is ground four times in a toothed attrition mill to give a pasty mixture that is refluxed for 10 hours. Next, the isobutanol is distilled off and, the pigment is filtered off and dried. A bluish-red pigment results that is well-suited for incorporation in lacquer systems and yields highly transparent dyeings of high gloss and good fastness properties.

EXAMPLE 2

100 Parts of 2,5-di-(4'-methylphenylamino)-terephthalic acid and 50 parts of 2,5-di-(3'-N-dimethylcarbamoylphenyl-amino)-terephthalic acid are added while stirring to 450 parts of polyphosphoric acid (about 83.5% of $P_2O_5$), at 110° to 120° and stirring is continued for 2 hours at 125°. The melt is hydrolyzed while stirring in water of 70°, the crude quinacridone is filtered off and washed acid-free with water. The crude quinacridone is stirred into 750 parts of ethanol and the weight of the mixture is made up to 1500 parts with water. Next, the suspension is ground twice in a colloid mill, then refluxed for 10 hours and, subsequently, the ethanol is distilled off while adding simultaneously water in such an amount that the volume remains constant. At 60° the pigment suspension is adjusted to slightly alkaline by adding a sodium carbonate solution, the suspension is stirred for 30 minutes, and the pigment is filtered off, washed neutral and dried at 80°.

The resulting bluish-red pigment can is suited for incorporation in lacquer systems. The highly transparent lacquer coatings exhibit a high gloss and good fastness properties.

EXAMPLE 3

A mixture of 140 parts of 2,5-di-(4'-methylphenylamino)-terephthalic acid and 40 parts of 2,5-di-(3'-carbamoyl-phenylamino)-terephthalic acid is cyclized in 450 parts of polyphosphoric acid and hydrolyzed in the manner described in Example 2. The neutral crude quinacridone is stirred into 900 parts of isobutanol (80%), and the mixture is made up to a total weight of 1500 parts with water and refluxed while stirring for 10 hours. Next, the isobutanol is distilled off with steam, the pigment suspension is adjusted to slightly alkaline with sodium carbonate solution, and the pigment is filtered off, washed and dried. The red-violet pigment is suitable for the pigmentation of lacquer systems. The lacquer coatings are very transparent and the lacquers are readily processed.

When replacing in the solvent treatment the isobutanol by methylisobutylketone or by acetone and when stirring in a closed vessel at 90° for 10 hours, there is obtained a similar product.

EXAMPLE 4

Into 150 parts of polyphosphoric acid (about 83.5% of $P_2O_5$) there are introduced while stirring 47 parts of 2,5-di-(4'-methylphenylamino)-terephthalic acid and 3 parts of 2,5-di-(4'-carbamoyl-phenylamino)-terephthalic acid at 120°, and stirring is continued for 2 hours at 125°. The melt is thereafter poured while stirring into 450 parts of 70°-hot water, wherein 3.5 parts of resin soap (50%) have been dissolved with addition of a slight amount of an alkali, and the mixture is stirred for 30 minutes. After standing for several hours the crude quinacridone is filtered off and washed acid-free with water. The neutral crude quinacridone is stirred into 250 parts of isobutanol (100%), and the weight of the suspension is made up to 500 parts with water, whereupon the suspension is ground intensely in a high-efficiency disperser for 5 minutes and refluxed for 10 hours while stirring. The alcohol is distilled off with steam, and the pigment is filtered off from the suspension, washed and dried. The bluish-red pigment can be readily processed in lacquers and has excellent fastness properties.

EXAMPLE 5

A mixture of 57.6 parts of 2,5-di-(40'-N-ethylcarbamoyl-phenylamino)-terephthalic acid and 115.2 parts of 2,5-di-(4'-methylphenylamino)-terephthalic acid is added while stirring to 600 parts of an acidic polyphosphoric acid methyl ester ($P_2O_5$ content about 80%), at 125° in 1 and a half hours. Stirring is continued for 2 hours at 130° C., whereupon the mixture is poured into a 70°-hot, slightly alkaline solution of 13 parts of resin soap (50%) and 1,800 parts of water, while stirring. The precipitated crude quinacridone is separated by filtration and washed neutral with water. The moist crude quinacridone is stirred into a mixture of 960 parts of water, 20 parts of potassium hydroxide and 400 parts of isobutanol (80%), ground twice in a colloid mill and subsequently stirred in a closed vessel for 5 hours at 125°. Next, the isobutanol is distilled off, and the pigment is filtered off, washed and dried. The red-violet pigment is distinguished by a pure shade, excellent fastness properties, high gloss and good transparency of the lacquer coatings produced therewith.

EXAMPLE 6

27 Parts of 2,5-di-(3'-N-methylcarbamoyl-phenylamino)-terephthalic acid and 150 parts of 2,5-di-(4'-methylphenyl-amino)-terephthalic acid are cyclized in 500 parts of polyphosphoric acid ($P_2O_5$ content about 83.5%), at 125°. The melt is hydrolyzed in 1,350 parts of water wherein 10 parts of resin soap (50%) have been dissolved with addition of a slight amount of an alkali. The crude quinacridone is isolated and washed acid-free with water.

The moist quinacridone is stirred in 720 parts of isobutanol (100%) and 180 parts of water in a closed vessel for 5 hours at 125°. After distilling off the isobutanol with steam, the pigment is isolated and dried.

The red-violet pigment is suitable for the pigmentation of lacquer systems. The lacquer coatings show a high transparency.

EXAMPLE 7

When proceeding as described in Example 6, with the exception that a mixture of 120 parts of 2,5-di-(4'-methylphenylamino)-terephthalic acid and 60 parts of 2,5-di-(4'-N-n-hexylcarbamoylphenylamino)-terephthalic acid is cyclized and that the isobutanolic crude quinacridone suspension is submitted to intensive grinding in a colloid mill, toothed attrition mill or agitator ball mill, prior to being heated to 125°, there is obtained a red-violet pigment of comparable quality.

EXAMPLE 8

50 Parts of 2,5-di-(4'-methylphenylamino)-terephthalic acid and 8.8 parts of 2,5-di-(4'-carbamoyl-phenylamino)-terephthalic acid are introduced into 150 parts of an acidic polyphosphoric acid methyl ester ($P_2O_5$ content about 80%) while stirring at 120° and the mixture is stirred for 2 hours at 125° to 130°. The cyclization product is thereafter poured into a stirred 70°-hot slightly alkaline solution of 450 parts of water and 3.5 parts of resin soap (50%). The precipitated crude quinacridone is filtered off and washed neutral. The moist crude quinacridone is stirred in 300 parts of isobutanol (80%) and the total of the suspension is made up to 500 parts with water. This suspension is ground intensively in a high-efficiency disperser and subsequently boiled for 10 hours. The isobutanol is removed with steam and the pigment is filtered off directly or after the addition of sodium hydroxide solution in such an amount that the suspension has a pH of 9, washed subsequently neutral with water and dried.

The bluish-red pigment has good rheological properties, yields transparent lacquer coatings and is very suitable for use in the automobile field.

The following corresponding quinacridone mixtures are obtained in the manner described in Example 8 by cyclization of the dianilinoterephthalic acid mixtures lised in the following Table. These mixtures have the same good properties as those obtained in Example 8.

TABLE

| Example No. | Mixture of diarylamino terephthalic acids (in parts by weight) | | Shade of the pigment |
|---|---|---|---|
| 9 | 50 | 2,5-di-(4'-methylphenylamino)-terephthalic acid | bluish-red |
| | 8.8 | 2,5-di-(3'-N—diethylcarbamoyl-phenylamino)-terephthalic acid | |
| 10 | 20 | 2,5-di-(4'-N—isobutylcarbamoyl-phenylamino)-terephthalic acid | " |
| | 40 | 2,5-di-(4'-methylphenylamino)-terephthalic acid | |
| 11 | 33.5 | 2,5-di-(4'-methylphenylamino)-terephthalic acid | red-violet |
| | 23.5 | 2,5-di-(4'-N—n-butylcarbamoyl-phenylamino)-terephthalic acid | |
| 12 | 50 | 2,5-di-(4'methylphenylamino)-terephthalic acid | bluish-red |
| | 8.8 | 2,5-di-(4'-diethylcarbamoyl-phenylamino)-terephthalic acid | |
| 13 | 50 | 2,5-di-(4'-methylphenylamino)-terephthalic acid | " |
| | 8.8 | 2,5-di-(4'-N—dimethylcarbamoyl-phenylamino)-terephthalic acid | |
| 14 | 45 | 2,5-diphenylamino-terephthalic acid | " |
| | 11 | 2,5-di-(4'-dimethylcarbamoyl- | |

| Example No. | Mixture of diarylamino terephthalic acids (in parts by weight) | Shade of the pigment |
|---|---|---|
| | phenylamino)-terephthalic acid | |
| 15 | 50  2,5-di-(4'-methylphenylamino)-terephthalic acid | " |
| | 9  2,5-di-(4'-N—n-propylcarbamoyl-phenylamino)-terephthalic acid | |
| 16 | 45  2,5-di-(4'-methyl-3'-chloro-phenyl-amino)-terephthalic acid | " |
| | 11  2,5-di-(4'-dimethylcarbamoyl-phenylamino)-terephthalic acid | |

EXAMPLE 17

A mixture of 7 parts of 2,5-di-(4'-chlorophenylamino)-terephthalic acid and 3 parts of 2,5-di-(4'carbamoylphenyl-amino)-terephthalic acid is cyclized in 70 parts of polyphosphoric acid ($P_2O_5$ content about 83.5%), at 125° to 135° followed by hydrolyzation in 225 parts of water of 70°. The isolated neutral water-moist crude quinacridone is suspended in 20 parts of ethanol and 40 parts of water, ground in a toothed attrition mill and stirred for 3 hours at 100°. Next, the ethanol is distilled off, the pH of the pigment suspension is adjusted to 9 with sodium hydroxide solution and the pigment is isolated, washed neutral and dried. The bluish-red pigment has excellent rheological properties and yields transparent lacquer coatings of excellent fastness properties.

EXAMPLE 18

10 Parts of 2,5-di-(3'-chlorophenylamino)-terephthalic acid and 2 parts of 2,5-di-(4'-carbamoylphenylamino)-terephthalic acid are cyclized at 130° in 60 parts of an acidic polyphosphoric acid methyl ester (about 81.5% of $P_2O_5$) and subsequently hydrolyzed. The isolated neutral crude quinacridone mixture is stirred in 60 parts of methanol and 300 parts of water and ground intensively in a high-efficiency disperser. The suspension is stirred for 3 hours at 110° in a closed vessel and cooled to 60°. Thereafter the methanol is distilled off, the pH of the mixture is adjusted to 9 with NaOH and, the pigment is isolated, washed neutral and dried. The red pigment can be readily processed and yields transparent lacquer coatings.

EXAMPLE 19

8.8 Parts of 2,5-di-(4'-N-methylcarbamoylphenylamino)-terephthalic acid and 50 parts of 2,5-di-(4'-methylphenyl-amino)-terephthalic acid are cyclized in the manner described in Example 8. The neutral moist crude quinacridone is stirred in 150 parts of isobutanol (80%), 150 parts of water and 10 parts of phosphoric acid (85%) for 16 hours at room temperature and boiled subsequently for 10 hours. The pigment isolated in the manner described in Example 8 is distinguished by a high transparency and good processability in lacquer systems.

What is claimed is:

1. A composition of matter comprising 30 to 95% of at least one component of the formula (I)

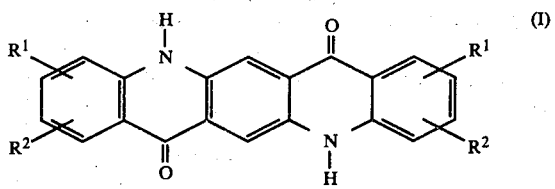

wherein $R^1$ and $R^2$ are the same or different and each is hydrogen, chlorine or methyl, and 5 to 70% of at least one component of the formula (II)

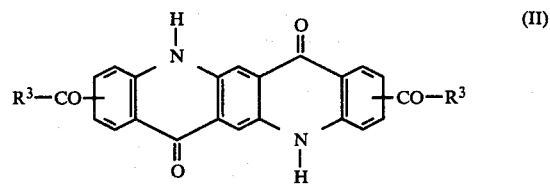

wherein $R^3$ is —NH—$R^4$ or —N($R^5$)$_2$, $R^4$ being hydrogen or alkyl of 1 to 6 carbon atoms and $R^5$ being methyl or ethyl.

2. A composition as claimed in claim 1, containing 30 to 95% by weight of component(s) (I) and 5 to 70% by weight of component(s) (II).
3. A composition as claimed in claim 1, containing 50 to 95% by weight of component(s) (I) and 5 to 50% by weight of component(s) (II).
4. A composition as claimed in claim 1, wherein component (I) is 2,9-dimethyl-quinacridone.
5. A composition as claimed in claim 4, wherein component (II) is a 2,9-bis-carbamoyl-quinacridone, the carbamoyl groups of which are unsubstituted, monosubstituted by ethyl, n-butyl or n-hexyl, or disubstituted by methyl.
6. A composition as claimed in claim 4, wherein component (II) is 2,9-bis-(carbamoyl)-quinacridone.
7. A composition as claimed in claim 4, wherein component (II) is 2,9-bis-(N-n-hexyl-carbamoyl)-quinacridone.
8. A composition as claimed in claim 4, wherein component (II) is 2,9-bis-(N-n-butyl-carbamoyl)-quinacridone.
9. A composition as claimed in claim 4, wherein component (II) is 2,9-bis-(N-ethyl-carbamoyl)-quinacridone.
10. A composition as claimed in claim 4, wherein component (II) is 2,9-bis-(N,N-dimethyl-carbamoyl)-quinacridone.
11. A composition as claimed in claim 4, wherein components (II) are a mixture of 3,10-, 1,8- and 1,10-bis-(N-methyl-carbamoyl)-quinacridone as obtained by ring-closure of 2,5-bis-m-(N-methyl-carbamoyl)-anilino terephthalic acid.
12. A composition as claimed in claim 6, consisting of 85% by weight of component (I) and of 15% by weight of component (II).
13. A composition as claimed in claim 7, consisting of about 66.7% by weight of component (I) and about 33.3% by weight of component (II).
14. A composition as claimed in claim 8, consisting of about 59% by weight of component (I) and about 41% by weight of component (II).
15. A composition as claimed in claim 9, consisting of about 66.7% by weight of component (I) and about 33.3% by weight of component (II).
16. A composition as claimed in claim 10, consisting of about 66.7% by weight of component (II) and about 33.3% by weight of component (I).
17. A composition as claimed in claim 11, consisting of about 84.5% by weight of component (I) and of about 15.5% by weight of the mixture of components (II).
18. A composition as claimed in claim 6, consisting of 94% by weight of component (I) and of 6% by weight of component (II).

* * * * *